(12) United States Patent
Lamego (10) Patent No.: US 9,119,595 B2
(45) Date of Patent: *Sep. 1, 2015

(54) REFLECTION-DETECTOR SENSOR POSITION INDICATOR

(71) Applicant: Masimo Corporation, Irvine, CA (US)

(72) Inventor: Marcelo M. Lamego, Cupertino, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/307,873

(22) Filed: Jun. 18, 2014

(65) Prior Publication Data

US 2014/0296720 A1 Oct. 2, 2014

Related U.S. Application Data

(63) Continuation of application No. 13/725,908, filed on Dec. 21, 2012, now Pat. No. 8,761,850, which is a continuation of application No. 12/577,670, filed on Oct. 12, 2009, now Pat. No. 8,346,330.

(60) Provisional application No. 61/104,969, filed on Oct. 13, 2008.

(51) Int. Cl.
*A61B 5/00* (2006.01)
*A61B 5/06* (2006.01)
(Continued)

(52) U.S. Cl.
CPC ............. *A61B 5/6844* (2013.01); *A61B 5/0205* (2013.01); *A61B 5/0261* (2013.01); *A61B 5/061* (2013.01); *A61B 5/1495* (2013.01); *A61B 5/14546* (2013.01); *A61B 5/14551* (2013.01); *A61B 5/14552* (2013.01); *A61B 5/6826* (2013.01); *A61B 5/6838* (2013.01); *A61B 5/743* (2013.01); *A61B 5/7405* (2013.01); *A61B 5/02416* (2013.01)

(58) Field of Classification Search
CPC ...................................................... A61B 5/1495
USPC .......................................... 600/310, 322, 323
See application file for complete search history.

(56) References Cited

U.S. PATENT DOCUMENTS

| 4,960,128 A | 10/1990 | Gordon et al. |
| 4,964,408 A | 10/1990 | Hink et al. |

(Continued)

OTHER PUBLICATIONS

US 8,845,543, 09/2014, Diab et al. (withdrawn)

*Primary Examiner* — Rodney Fuller
(74) *Attorney, Agent, or Firm* — Knobbe, Martens, Olson & Bear LLP (57) ABSTRACT

A reflection-detector sensor position indicator comprises emitters that transmit light having a plurality of wavelengths. A detector outputs a sensor signal. At least one reflection detector outputs at least one sensor position signal. An attachment assembly attaches the emitters, the detector and the reflection detector onto a tissue site. A sensor-on condition indicates that the attachment assembly has positioned the emitters generally centered over a fingernail, the detector on a fingertip opposite the fingernail and the reflection detector over the fingernail. The sensor signal, in the sensor-on condition, is at least substantially responsive to the emitter transmitted light after attenuation by pulsatile blood flow perfused within a fingernail bed underneath the fingernail. The sensor position signal, in the sensor-on condition, is at least substantially responsive to the emitter transmitted light after reflection off of the fingernail.

12 Claims, 5 Drawing Sheets

(51) Int. Cl.

| | |
|---|---|
| A61B 5/1455 | (2006.01) |
| A61B 5/0205 | (2006.01) |
| A61B 5/026 | (2006.01) |
| A61B 5/145 | (2006.01) |
| A61B 5/1495 | (2006.01) |
| A61B 5/024 | (2006.01) |

(56) References Cited

U.S. PATENT DOCUMENTS

| | | | |
|---|---|---|---|
| 5,041,187 A | 8/1991 | Hink et al. | |
| 5,069,213 A | 12/1991 | Polczynski | |
| 5,163,438 A | 11/1992 | Gordon et al. | |
| 5,278,627 A * | 1/1994 | Aoyagi et al. | 600/331 |
| 5,319,355 A | 6/1994 | Russek | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |
| 5,479,934 A | 1/1996 | Imran | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,534,851 A | 7/1996 | Russek | |
| 5,561,275 A | 10/1996 | Savage et al. | |
| 5,562,002 A | 10/1996 | Lalin | |
| 5,588,427 A | 12/1996 | Tien | |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,823,950 A | 10/1998 | Diab et al. | |
| 5,830,131 A | 11/1998 | Caro et al. | |
| 5,833,618 A | 11/1998 | Caro et al. | |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,045,509 A | 4/2000 | Caro et al. | |
| 6,067,462 A | 5/2000 | Diab et al. | |
| 6,081,735 A | 6/2000 | Diab et al. | |
| 6,088,607 A | 7/2000 | Diab et al. | |
| 6,110,522 A | 8/2000 | Lepper, Jr. et al. | |
| 6,124,597 A | 9/2000 | Shehada | |
| 6,128,521 A | 10/2000 | Marro et al. | |
| 6,129,675 A | 10/2000 | Jay | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,232,609 B1 | 5/2001 | Snyder et al. | |
| 6,236,872 B1 | 5/2001 | Diab et al. | |
| 6,241,683 B1 | 6/2001 | Macklem et al. | |
| 6,253,097 B1 | 6/2001 | Aronow et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,301,493 B1 | 10/2001 | Marro et al. | |
| 6,317,627 B1 | 11/2001 | Ennen et al. | |
| 6,321,100 B1 | 11/2001 | Parker | |
| 6,325,761 B1 | 12/2001 | Jay | |
| 6,334,065 B1 | 12/2001 | Al-Ali et al. | |
| 6,343,224 B1 | 1/2002 | Parker | |
| 6,349,228 B1 | 2/2002 | Kiani et al. | |
| 6,360,114 B1 | 3/2002 | Diab et al. | |
| 6,368,283 B1 | 4/2002 | Xu et al. | |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,397,091 B2 | 5/2002 | Diab et al. | |
| 6,430,437 B1 | 8/2002 | Marro | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,501,975 B2 | 12/2002 | Diab et al. | |
| 6,505,059 B1 | 1/2003 | Kollias et al. | |
| 6,515,273 B2 | 2/2003 | Al-Ali | |
| 6,519,487 B1 | 2/2003 | Parker | |
| 6,525,386 B1 | 2/2003 | Mills et al. | |
| 6,526,300 B1 | 2/2003 | Kiani et al. | |
| 6,541,756 B2 | 4/2003 | Schulz et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,595,316 B2 | 7/2003 | Cybulski et al. | |
| 6,597,932 B2 | 7/2003 | Tian et al. | |
| 6,597,933 B2 | 7/2003 | Kiani et al. | |
| 6,606,511 B1 | 8/2003 | Ali et al. | |
| 6,632,181 B2 | 10/2003 | Flaherty et al. | |
| 6,639,668 B1 | 10/2003 | Trepagnier | |
| 6,640,116 B2 | 10/2003 | Diab | |
| 6,643,530 B2 | 11/2003 | Diab et al. | |
| 6,650,917 B2 | 11/2003 | Diab et al. | |
| 6,654,624 B2 | 11/2003 | Diab et al. | |
| 6,658,276 B2 | 12/2003 | Kianl et al. | |
| 6,661,161 B1 | 12/2003 | Lanzo et al. | |
| 6,671,531 B2 | 12/2003 | Al-Ali et al. | |
| 6,678,543 B2 | 1/2004 | Diab et al. | |
| 6,684,090 B2 | 1/2004 | Ali et al. | |
| 6,684,091 B2 | 1/2004 | Parker | |
| 6,697,656 B1 | 2/2004 | Al-Ali | |
| 6,697,657 B1 | 2/2004 | Shehada et al. | |
| 6,697,658 B2 | 2/2004 | Al-Ali | |
| RE38,476 E | 3/2004 | Diab et al. | |
| 6,699,194 B1 | 3/2004 | Diab et al. | |
| 6,714,804 B2 | 3/2004 | Al-Ali et al. | |
| RE38,492 E | 4/2004 | Diab et al. | |
| 6,721,582 B2 | 4/2004 | Trepagnier et al. | |
| 6,721,585 B1 | 4/2004 | Parker | |
| 6,725,075 B2 | 4/2004 | Al-Ali | |
| 6,728,560 B2 | 4/2004 | Kollias et al. | |
| 6,735,459 B2 | 5/2004 | Parker | |
| 6,745,060 B2 | 6/2004 | Diab et al. | |
| 6,760,607 B2 | 7/2004 | Al-Ali | |
| 6,770,028 B1 | 8/2004 | Ali et al. | |
| 6,771,994 B2 | 8/2004 | Kiani et al. | |
| 6,792,300 B1 | 9/2004 | Diab et al. | |
| 6,813,511 B2 | 11/2004 | Diab et al. | |
| 6,816,741 B2 | 11/2004 | Diab | |

(56) References Cited

U.S. PATENT DOCUMENTS

| | | |
|---|---|---|
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |

(56) References Cited

U.S. PATENT DOCUMENTS

| | | |
|---|---|---|
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 * | 1/2013 | Lamego .................. 600/322 |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 * | 4/2014 | Kiani ..................... 600/310 |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 * | 6/2014 | Lamego .................. 600/322 |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |

(56) References Cited

U.S. PATENT DOCUMENTS

| | | |
|---|---|---|
| 8,996,085 B2 | 3/2015 | Kiani et al. |
| 8,998,809 B2 | 4/2015 | Kiani |
| 2003/0139656 A1* | 7/2003 | Kiani et al. .................. 600/322 |
| 2006/0009685 A1 | 1/2006 | Finarov et al. |
| 2006/0178580 A1 | 8/2006 | Nakamura et al. |
| 2006/0220881 A1 | 10/2006 | Al-Ali et al. |
| 2008/0122803 A1 | 5/2008 | Izadi et al. |
| 2009/0018417 A1 | 1/2009 | Wang |
| 2009/0027358 A1 | 1/2009 | Hosono |
| 2009/0247984 A1 | 10/2009 | Lamego et al. |
| 2009/0275844 A1 | 11/2009 | Al-Ali |
| 2009/0299157 A1 | 12/2009 | Telfort et al. |
| 2010/0004518 A1 | 1/2010 | Vo et al. |
| 2010/0030040 A1 | 2/2010 | Poeze et al. |
| 2010/0261979 A1 | 10/2010 | Kiani |
| 2011/0001605 A1 | 1/2011 | Kiani et al. |
| 2011/0082711 A1 | 4/2011 | Poeze et al. |
| 2011/0105854 A1 | 5/2011 | Kiani et al. |
| 2011/0208015 A1 | 8/2011 | Welch et al. |
| 2011/0209915 A1 | 9/2011 | Telfort et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2012/0059267 A1 | 3/2012 | Lamego et al. |
| 2012/0116175 A1 | 5/2012 | Al-Ali et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0265039 A1 | 10/2012 | Kiani |
| 2012/0283524 A1 | 11/2012 | Kiani et al. |
| 2012/0286955 A1 | 11/2012 | Welch et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060108 A1 | 3/2013 | Schurman et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0162433 A1 | 6/2013 | Muhsin et al. |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0274571 A1 | 10/2013 | Diab et al. |
| 2013/0296672 A1 | 11/2013 | O'Neil et al. |
| 2013/0317370 A1 | 11/2013 | Dalvi et al. |
| 2013/0324808 A1 | 12/2013 | Al-Ali et al. |
| 2013/0331670 A1 | 12/2013 | Kiani |
| 2013/0338461 A1 | 12/2013 | Lamego et al. |
| 2014/0012100 A1 | 1/2014 | Al-Ali et al. |
| 2014/0025306 A1 | 1/2014 | Weber et al. |
| 2014/0034353 A1 | 2/2014 | Al-Ali et al. |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0125495 A1 | 5/2014 | Al-Ali |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200420 A1 | 7/2014 | Al-Ali |
| 2014/0200422 A1 | 7/2014 | Weber et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0309559 A1 | 10/2014 | Telfort et al. |
| 2014/0316228 A1 | 10/2014 | Blank et al. |
| 2014/0323825 A1 | 10/2014 | Al-Ali et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2015/0018650 A1 | 1/2015 | Al-Ali et al. |

* cited by examiner

REFLECTION-DETECTOR SENSOR POSITION INDICATOR

CROSS-REFERENCE TO RELATED APPLICATIONS

The present application is a continuation of U.S. patent application Ser. No. 13/725,908, filed Dec. 21, 2012, now U.S. Pat. No. 8,761,850, titled Reflection-Detector Sensor Position Indicator, which is a continuation of U.S. patent application Ser. No. 12/577,670, filed Oct. 12, 2009, now U.S. Pat. No. 8,346,330, titled Reflection-Detector Sensor Position Indicator, which claims priority benefit under 35 U.S.C. §119(e) to U.S. Provisional Patent Application Ser. No. 61/104,969, filed Oct. 13, 2008, titled Reflection-Detector Sensor Position Indicator, hereby incorporated by reference herein.

BACKGROUND

Pulse oximetry is a technique that utilizes a noninvasive sensor to determine a person's oxygen status. An optical sensor used in pulse oximetry has light emitting diodes (LEDs) that transmit optical radiation of red and infrared wavelengths into a tissue site. A detector in the sensor responds to the intensity of the optical radiation after attenuation by pulsatile arterial blood flowing within the tissue site. Based on this response, a processor determines measurements for $SpO_2$ and pulse rate among other parameters. Pulse oximeters capable of reading through motion induced noise are available from Masimo Corporation ("Masimo") of Irvine, Calif. Moreover, portable and other pulse oximeters capable of reading through motion induced noise are disclosed in at least U.S. Pat. Nos. 6,770,028, 6,658,276, 6,157,850, 6,002,952, 5,769,785 and 5,758,644, which are owned by Masimo and are incorporated by reference herein. Corresponding low noise optical sensors are also available from Masimo and are disclosed in at least U.S. Pat. Nos. 6,985,764, 6,813,511, 6,792,300, 6,256,523, 6,088,607, 5,782,757 and 5,638,818. Such reading through motion pulse oximeters and low noise sensors have gained rapid acceptance in a wide variety of medical applications, including surgical wards, intensive care and neonatal units, general wards, home care, physical training, and virtually all types of monitoring scenarios. Moreover, pulse oximeters capable of reading through motion induced noise and low noise optical sensors including LNOP® disposable, reusable and/or multi-site sensors and Radical®, Rad-5™, Rad-8™, Rad-9™, PPO+™ monitors are also available from Masimo.

Further, noninvasive blood parameter monitors capable of measuring parameters in addition to $SpO_2$, such as HbCO, HbMet and Hbt, and corresponding multiple wavelength optical sensors are also available from Masimo. Noninvasive blood parameter monitors and corresponding multiple wavelength optical sensors are described in at least U.S. patent application Ser. No. 11/367,013, filed Mar. 1, 2006, titled Multiple Wavelength Sensor Emitters and U.S. patent application Ser. No. 11/366,208, filed Mar. 1, 2006, titled Noninvasive Multi-Parameter Patient Monitor, both assigned to Masimo Laboratories, Irvine, Calif. (Masimo Labs) and both incorporated by reference herein. Moreover, multiple parameter monitors and multiple wavelength sensors including Rad-57™ and Radical-7™ monitors and Rainbow™ Rainbow™-brand adhesive and reusable sensors are available from Masimo. MS- and MX-brand processor boards are also available from Masimo.

SUMMARY

Problems arise if a pulse oximeter or other blood parameter monitor is connected to an optical sensor that is not properly positioned on a tissue site or becomes partially or completely dislodged from a patient, a so-called "probe off" condition. When an optical sensor is properly positioned on a tissue site, the detector only receives LED emitted light that has propagated via the tissue site to the detector after tissue scattering and absorption. Thus, the AC detector signal that results accurately reflects the differential absorption of constituents in the pulsatile arterial blood, as described above. If a sensor is off a tissue site or is mis-positioned on the tissue site, the detector may directly receive LED emitted light, i.e. light that has not propagated through any tissue. Despite a probe-off condition, a blood parameter monitor may continue to detect an AC signal, which can be induced at the detector by other than pulsatile arterial attenuation of LED emitted light. Small patient movements, vibrations, air flow or other perturbations may cause the pathlength between the LEDs and detector to vary, resulting in an AC detector signal that can be mistakenly interpreted by the monitor as due to pulsatile arterial blood. Further, ambient light may reach the detector, and any modulation of the ambient light due to AC power, power fluctuations, moving objects, such as a fan, among other perturbations can also be mistaken as a pulsatile arterial signal. Probe-off errors are serious because a blood parameter monitor may still display a normal measurement, potentially leading to critical missed events, such as a patient desaturation.

An aspect of an optical sensor comprises emitters that transmit light having a plurality of wavelengths. A detector outputs a sensor signal. At least one reflection detector outputs at least one sensor position signal. An attachment assembly attaches the emitters, the detector and the reflection detector onto a tissue site. A sensor-on condition indicates that the attachment assembly has positioned the emitters generally centered over a fingernail, the detector on a fingertip opposite the fingernail and the reflection detector over the fingernail. The sensor signal, in the sensor-on condition, is at least substantially responsive to the emitter transmitted light after attenuation by pulsatile blood flow perfused within a fingernail bed underneath the fingernail. The sensor position signal, in the sensor-on condition, is at least substantially responsive to the emitter transmitted light after reflection off of the fingernail.

In various embodiments, the optical sensor has a first reflection detector and a second reflection detector that generate a first sensor position signal and a second sensor position signal in response to reflected light from the emitters. The first reflection detector and the second reflection detector are positioned on opposite sides of the emitters. The magnitudes of the first sensor position signal and the second sensor position signal each have values within a sensor-on range of values during a sensor-on condition. At least one of the magnitudes of the first sensor position signal and the second sensor position signal have values within a sensor mis-positioned range of values when an attachment assembly positions the emitters partially off the center of the fingernail. The magnitudes of the first sensor position signal and the second sensor position signal each have values within a sensor-off range of values when the attachment assembly positions the emitters substantially off of the fingernail. The magnitude of the first sensor position signal has values in a mis-positioned range of values and the magnitude of the second position signal having values in a sensor-on range of values when the attachment assembly positions the emitters in a sensor over-positioned condition partially off-center of the fingernail and proximate the fingertip. The magnitude of the first sensor position signal has values in a sensor-on range of values and the magnitude of the second sensor position signal has values in a mis-positioned range of values when the attachment assembly positions the emitters off-center of the fingernail and distal the fingertip in a sensor under-positioned condition.

An aspect of a sensor position indicator comprises activating emitters with an emitter activation signal so as to transmit light, receiving a sensor position signal from a reflection detector responsive to reflections of the transmitted light, and indicating a sensor attachment condition in response to the sensor position signal. In various embodiments, the magnitude of the sensor position signal is determined with respect to at least one of a sensor-on range of values and a sensor mis-positioned range of values. A second sensor position signal is received from a second reflection detector responsive to reflections of the transmitted light. The magnitude of the second sensor position signal is determined with respect to at least one of a sensor-on range of values and a sensor mis-positioned range of values. The magnitude of the sensor position signal is compared to the magnitude of the second sensor position signal so as to determine at least one of a sensor over-positioned range of values, a sensor under-positioned range of values and a sensor-off range of values. A monitor display graphically depicts at least multiple ones of a sensor-on condition, a sensor-off condition, a sensor over-positioned condition and a sensor under-positioned condition.

An aspect of a physiological measurement system comprises a sensor having an attachment assembly configured to position emitters over a fingernail and to position a detector on a fingertip opposite the fingernail so that the emitters are positioned to transmit multiple wavelength light into the fingernail and so that the detector is positioned to detect the transmitted light after attenuation by pulsatile blood flow perfused within a fingernail bed underneath the fingernail and generate a sensor signal responsive to the intensity of the detected light. A second detector incorporated within the sensor generates a sensor position signal responsive to the position of the emitters over the fingernail. A physiological monitor is in communications with the sensor so as to drive the emitters, receive the corresponding sensor signal from the detector, and receive the corresponding sensor position signal from the second detector. The physiological monitor derives physiological parameters from the sensor signal and derives a sensor position indicator from the sensor position signal.

In various embodiments, the physiological measurement system comprises a third detector incorporated within the sensor that generates a second sensor position signal responsive to the position of the emitters over the fingernail. The physiological monitor derives multiple ones of a sensor-on condition, a sensor-off condition and a sensor mis-positioned condition from the sensor position signal and the second sensor position signal. The physiological monitor derives a sensor under-positioned condition and a sensor over-positioned condition from the sensor position signals. The physiological monitor generates a display that depicts the position of a finger relative to the sensor so as to visually indicate multiple ones of a sensor-on condition, a sensor-off condition, a sensor under-positioned condition and a sensor over-positioned condition. The physiological measurement system comprises an audible indicator of multiple ones of a sensor-on condition, a sensor-off condition, a sensor under-positioned condition and a sensor over-positioned condition.

A further aspect of a sensor position indicator comprises an emitter means for transmitting light into a tissue site so as to determine physiological parameters derived from detection of the light after attenuation by pulsatile blood flow within the tissue site, a reflection detection means for generating a sensor position signal responsive to reflections of the transmitted light, and a processor means for determining a sensor position condition from the magnitude of the sensor position signal. An embodiment further comprises a display means for indicating the sensor position condition. The reflection detection means may comprise a first reflection detector means and a second reflection detector means located relative to the emitter means so as to determine a sensor over-positioned condition, a sensor under-positioned condition and a sensor-off condition. The processor means may comprise a calculation means for determining a first signal magnitude from the first reflection detector means and a second signal magnitude from the second signal magnitude. The process means may further comprises a comparator means for comparing the first signal magnitude and the second signal magnitude to each other and to ranges of sensor position values.

DETAILED DESCRIPTION OF THE PREFERRED EMBODIMENTS

Figure 1:
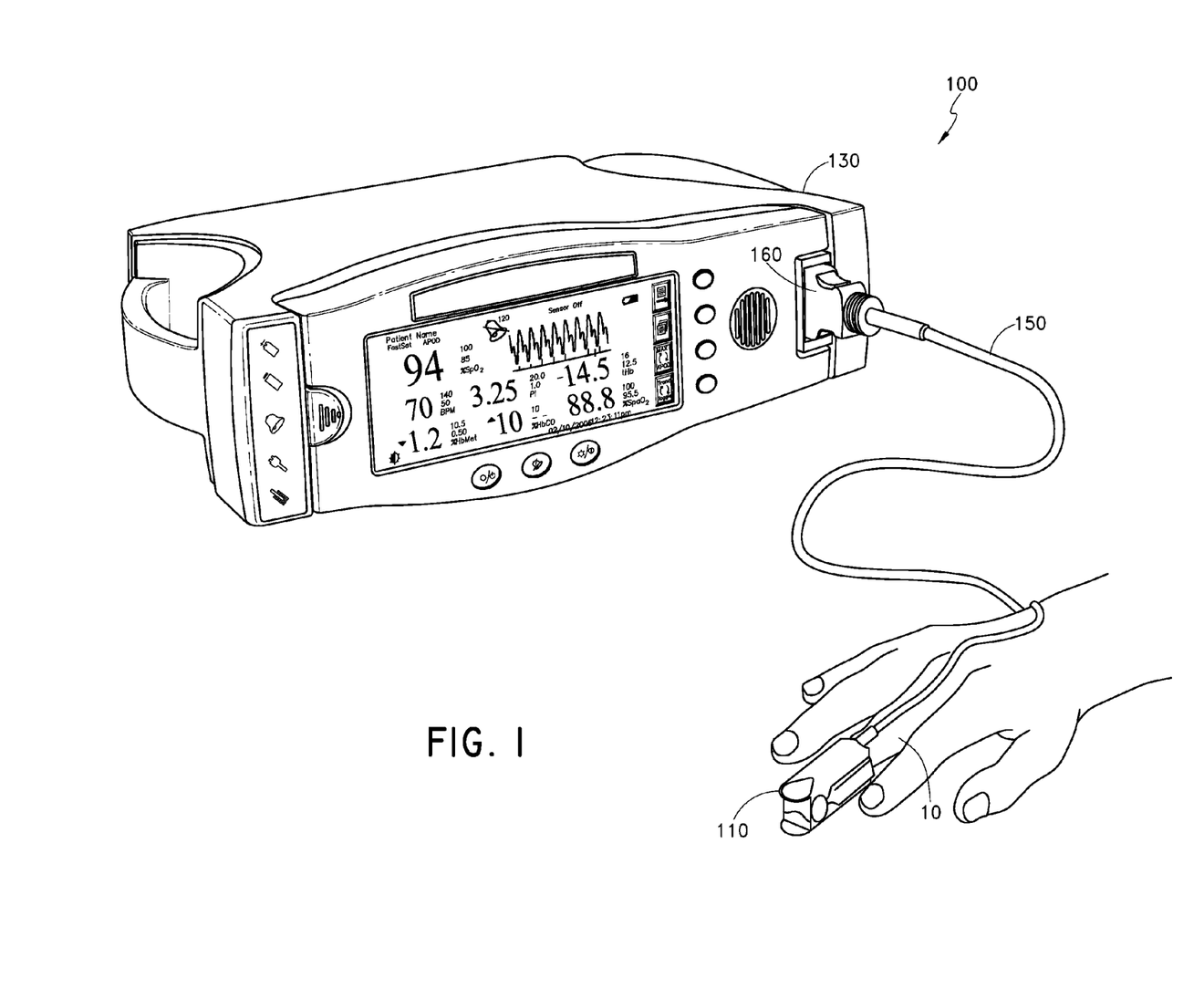
FIG. 1 is a perspective illustration of a physiological measurement system utilizing a reflection-detector sensor position indicator.
Figure 2:
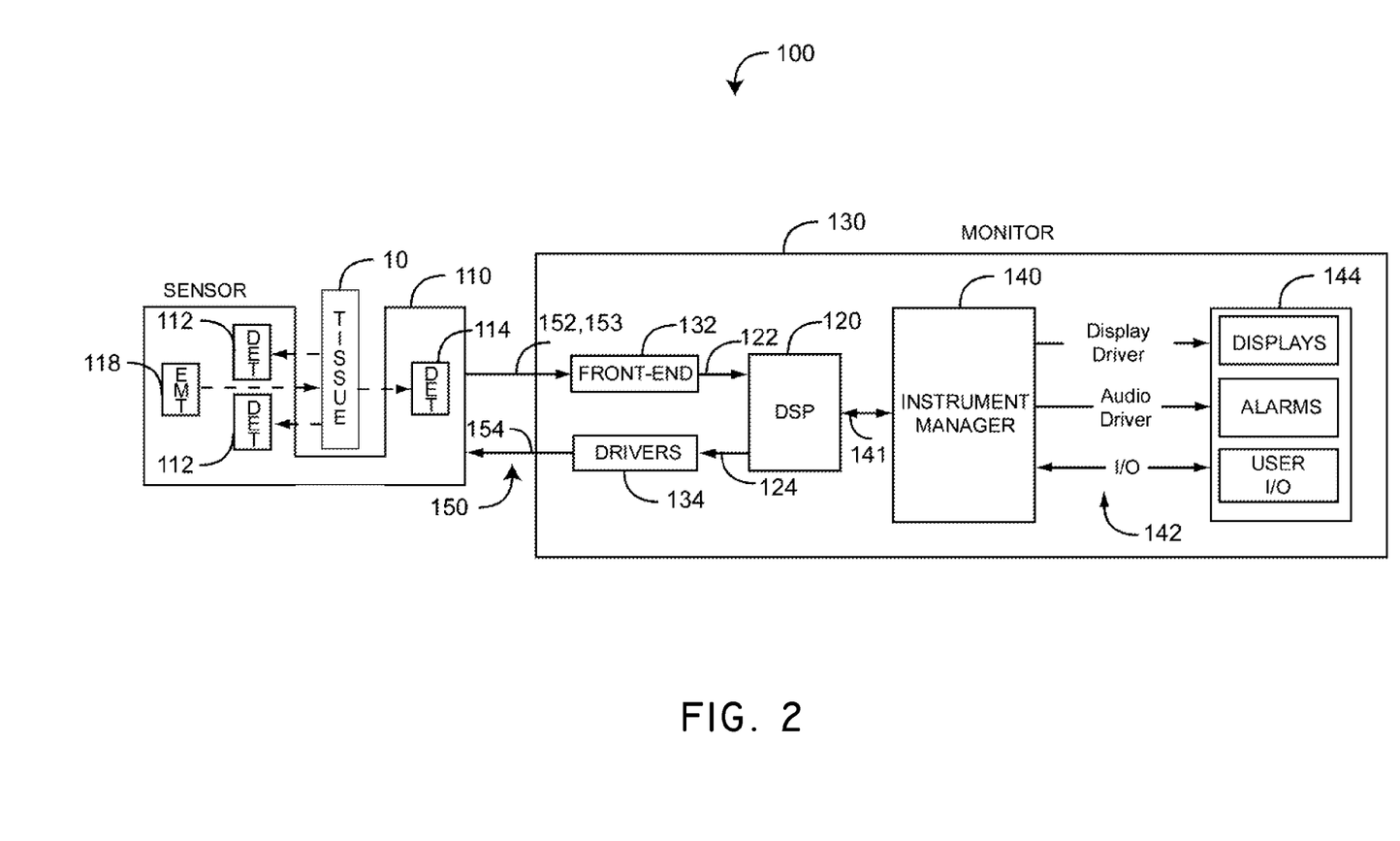
FIG. 2 is a block diagram of a physiological measurement system utilizing a reflection-detector sensor position indicator.

FIGS. 1-2 illustrate a physiological measurement system 100 which measures blood constituents and related parameters, such as oxygen saturation, pulse rate, perfusion index (PI), pleth variability index (PVI™), HbCO, HbMet and Hbt, to name a few. The physiological measurement system 100 includes an optical sensor 110 applied to a tissue site 10, a physiological monitor 130 and a cable 150 that physically and electrically connects the sensor 110 to the monitor 130. Advantageously, the physiological measurement system 100 also utilizes a sensor position indicator responsive to improper placement of the sensor 110 on a finger or other tissue site 10, as described in detail below.

As shown in FIGS. 1-2, the monitor 130 communicates with the sensor 110 to receive one or more sensor signals indicative of one or more physiological parameters. In particular, a digital signal processor (DSP) 120 outputs digital control signals 124 to drivers 134 and inputs digital data 122 from the front-end 132. The drivers 134 convert the digital control signals 124 into analog drive signals 154 capable of driving sensor emitters 118, which transmit optical radiation having multiple wavelengths into a tissue site 10. A primary detector 114 responds to the intensity of the optical radiation after attenuation by pulsatile blood flow within the tissue site 10 and generates a corresponding sensor signal 152. The front-end 132 converts the analog sensor signal 152 into the input digital data 122 to the DSP 120. The DSP 120 comprises any of a wide variety of data and signal processors capable of executing programs for determining physiological parameters from input data. The instrument manager 140, which may comprise one or more microcontrollers, has communications 141 with the DSP 120, such as to monitor activity of the DSP 138 and download calculated parameters. The instrument manager 140 also has communications 142 with displays, alarms and user input/output (I/O) 144. In an embodiment, a display 144 depicts the position of a finger relative to the sensor according to any of a sensor on, sensor off and sensor mis-positioned condition.

Also shown in FIG. 2, in an embodiment, a sensor position indicator incorporates one or more reflection detectors 112 located inside the sensor 110. The reflection detectors 112 generate sensor position signals 153 that are responsive to the emitter 118 being properly positioned over a fingernail bed and the corresponding high reflectivity of a fingernail. In this manner, a sensor position signal 153 that are weakly or non-responsive to the emitter 118 are indicative of a sensor-off or a sensor mis-positioned condition, as described in further detail with respect to FIGS. 3A-B, below.

Figure 3A:
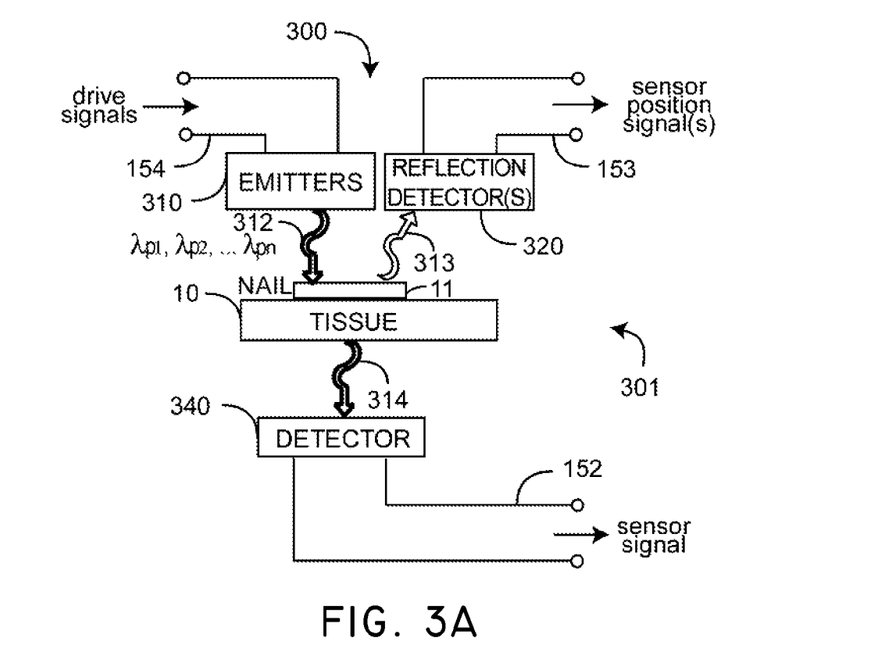
FIGS. 3A-B are general block diagrams of a reflection-detector sensor position indicator illustrating sensor-on and sensor-off conditions, respectively.
Figure 3B:
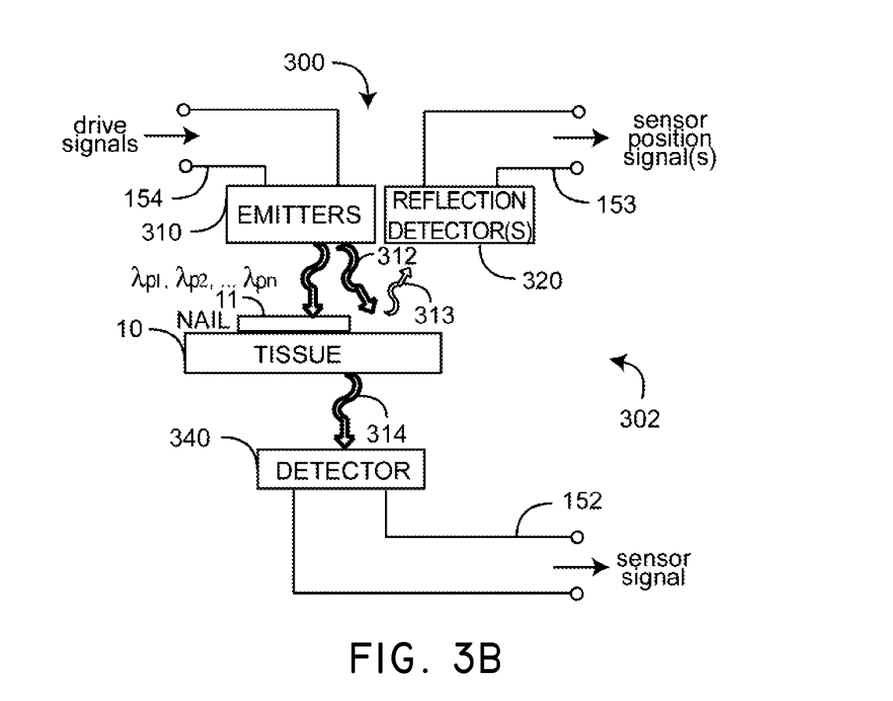

FIGS. 3A-B illustrate a sensor 300 having one or more reflection detectors 320 configured for sensor position indication. The sensor 300 has emitters 310 capable of transmitting light having wavelengths ($\lambda_p$) 312 into a tissue site 10 in response to a drive signals 154. A detector 340 detects the transmitted light 312 after attenuation by the tissue site 10 and outputs a sensor signal 152 responsive to the tissue-attenuated light 314. The sensor signal 152 is indicative of at least one physiological parameter corresponding to the tissue site 10. Advantageously, the sensor 300 has at least one reflection detector 320 that detects reflected light 313 from a nail 11 and outputs a sensor position signal 153 responsive to the nail-reflected light 313. The sensor position signal 153 is indicative of sensor position, as described in further detail below. A monitor 130 (FIG. 2) is in communications with the sensor 300 via the drive signals 154 and the corresponding sensor signal 152 and sensor position signal 153.

As shown in FIG. 3A, a sensor-on condition 301 is where the tissue site 10 is properly placed relative to the detector 340 so that accurate physiological measurements can be made. In particular, an emitter 310 is placed so as to substantially illuminate a blood-perfused nail bed underneath a fingernail 11. For example, in a sensor-on condition 301, the reflection detector 320 receives emitted light 312 after reflection 313 from the relatively reflective surface of a fingernail 11 and generates a relatively large AC and DC sensor position signal 153 accordingly.

As shown in FIG. 3B, a sensor mis-positioned condition or a sensor-off condition 302 is where the tissue site 10 is displaced relative to the emitters 310, so that the emitters do not illuminate a substantial portion of a nail bed. For example, in a sensor mis-positioned condition or a sensor-off condition 302, the reflection detector 320 receives emitted light 312 after reflection 313 from a relatively non-reflective surface, such as skin surrounding the fingernail 11 and generates a relatively small AC and DC secondary sensor signal 152 accordingly. Various embodiments of a sensor position indicator utilizing a reflection detector is described with respect to FIGS. 4-5, below.

FIGS. 4A-D illustrate a reflection detector sensor 400 having emitters 410, such as emitters 310 (FIGS. 3A-B), a detector 420, such as a detector 340 (FIGS. 3A-B) and at least one reflection detector 430, 440, such as reflection detectors 320 (FIGS. 3A-B). The reflection detector sensor 400 has an insertion end 12 that accepts a fingertip or, generally, insertion of a tissue site. Advantageously, the reflection detectors 430, 440 are capable of distinguishing a sensor-on condition 405, a sensor under-positioned condition 406, a sensor over-positioned condition 407 and a sensor-off condition 408.

Figure 4A:
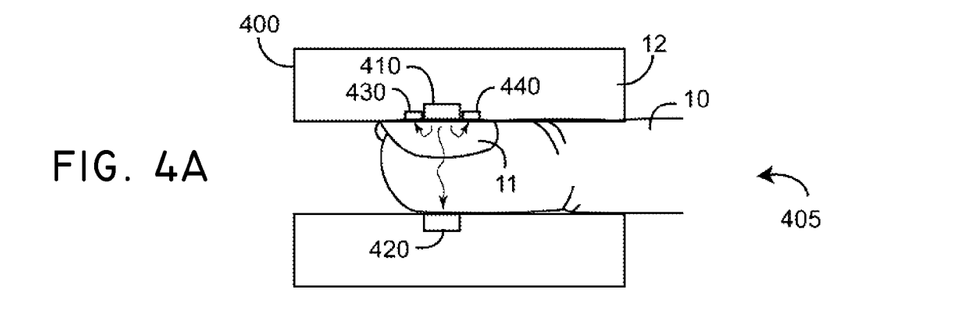
FIGS. 4A-D are side view illustrations of a reflection-detector sensor position indicator illustrating sensor-on, sensor under-positioned, sensor over-positioned and sensor-off conditions, respectively.

As shown in FIG. 4A, in a sensor-on condition 405, a fingertip is placed the proper distance into the sensor from the insertion end 12 so that both reflection detectors 430, 440 detect the increased reflectivity of emitted light from the emitters 410 positioned squarely over the fingernail 11. In the sensor-on condition 405, the emitters 410 transmit light directly into the blood-perfused nail bed underneath the fingernail 11.

Figure 4B:
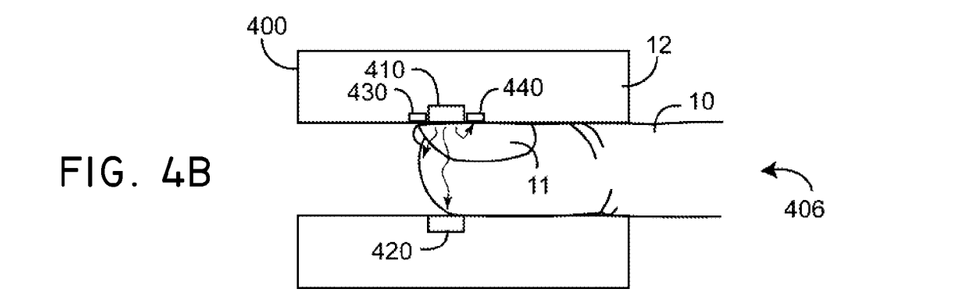

As shown in FIG. 4B, in a sensor under-positioned condition 406, a finger 10 is not inserted far enough into the reflection-detector sensor 400. As a result, the emitters 410 are positioned at least partially away from the center of the fingernail 11 and, accordingly, are only able to partially transmit light into the fingernail bed. Further, a first reflection detector 430 distal the insertion end 12 is also distal the center of the fingernail so that it detects a reduced light intensity compared to a second reflection detector 440 proximate the insertion end 12.

Figure 4C:
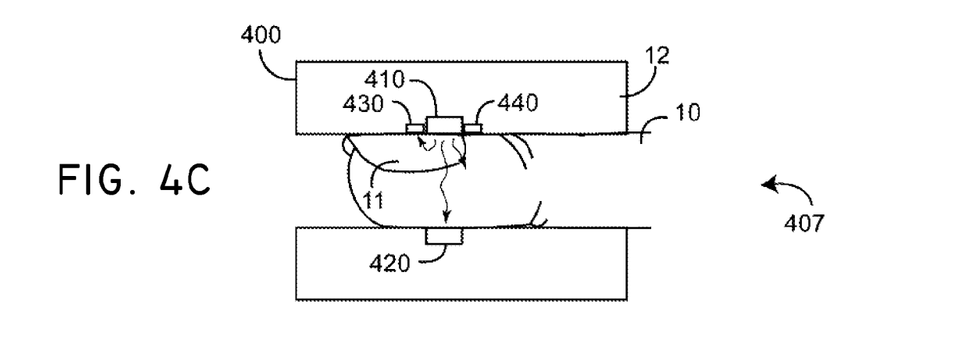

As shown in FIG. 4C, in a sensor over-positioned condition 407, a finger 10 is inserted too far into the reflection-detector sensor 400. Similar to the sensor under-positioned condition 406, this results in the emitters 410 being positioned at least partially away from the center of the fingernail 11 and only partially able to transmit light into the fingernail bed. Further, a second reflection detector 440 proximate the insertion end 12 is distal the center of the fingernail 11 so that it detects a reduced light intensity compared to a first reflection detector 430 distal the insertion end 12.

Figure 4D:
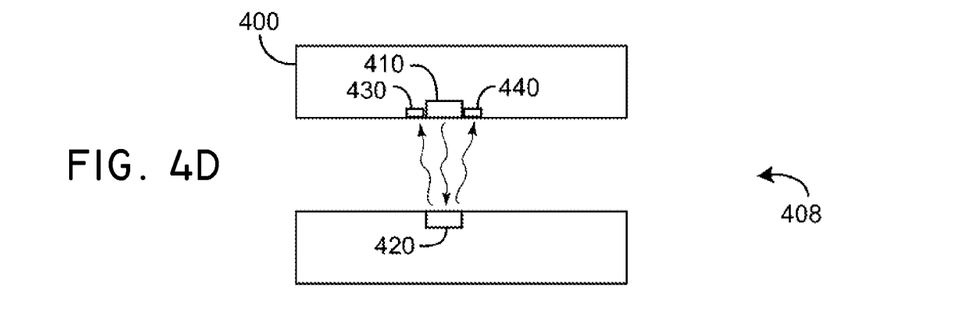

As shown in FIG. 4D, in a sensor-off condition 408, the sensor 400 is significantly misplaced on a fingertip or completely removed from a finger 10. Accordingly, the reflection detectors 430, 440 both detect the reduced reflectivity of the emitters 410 positioned over an air gap and the opposite side of the sensor 400 compared with emitters 410 positioned over a fingernail 11 as in the sensor-on condition 405 (FIG. 4A).

Figure 5A:
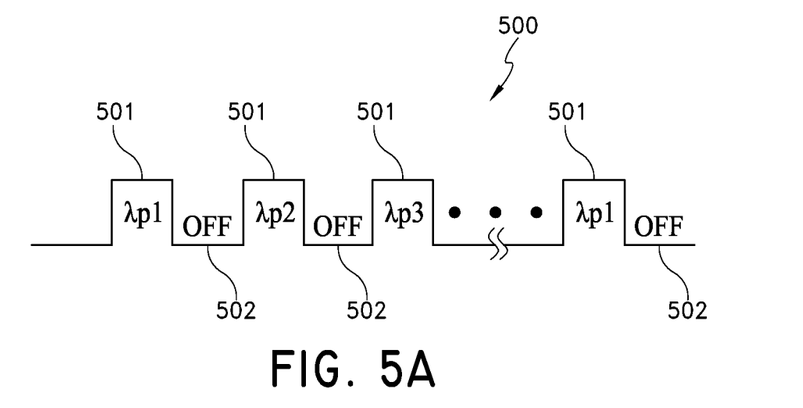
FIGS. 5A-C are timing diagrams for a reflection-detector sensor position indicator illustrating emitter drive signals and corresponding reflection-detector output signals related to high-reflectivity and low-reflectivity surfaces, respectively.
Figure 5B:
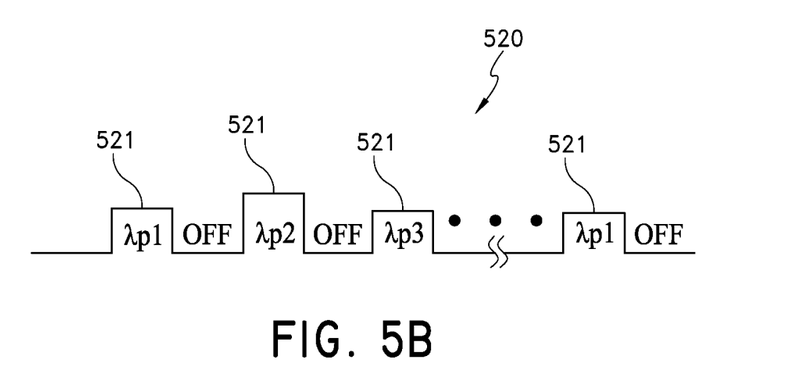
Figure 5C:
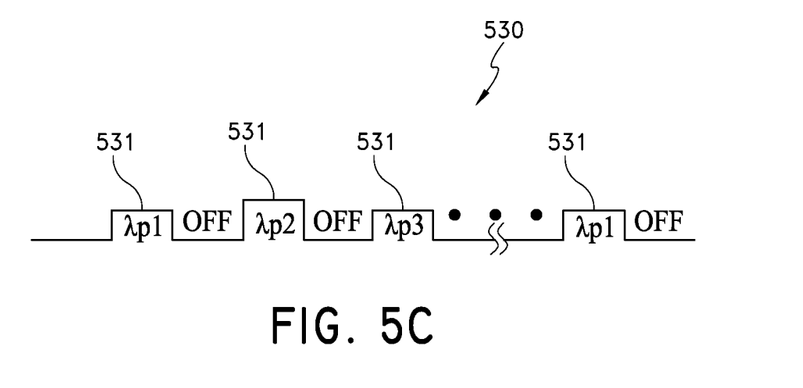

FIGS. 5A-C illustrate timing diagrams 500-530 for emitter drive currents, such as from monitor drive signals 154 (FIGS. 3A-B) and corresponding reflection detector response currents, such as to generate sensor position signals 153 (FIGS. 3A-B). As shown in FIG. 5A, emitter drive currents 500 have drive periods 501 and off periods 502 for each emitted wavelength $\lambda_{pi}$. FIG. 5B illustrates a relatively large reflection detector response 520 corresponding to a high-reflectivity surface. Specifically, the on periods 521 corresponding to the emitter drive periods 501 (FIG. 5A) indicate that emitted light is reflected off a nail surface and received by a reflection detector 430, 440 (FIG. 4A). FIG. 5C illustrates a relatively small reflection detector response 530 corresponding to a low-reflectivity surface. Specifically, the on periods 531 corresponding to the emitter drive periods 501 (FIG. 5A) indicate that emitted light is reflected off a relatively low reflectivity skin-surface or sensor-surface and received by a reflection detector 430, 440 (FIG. 4A). A monitor 130 (FIG. 2) determines which reflection detectors 430, 440 (FIG. 4A) receive the emitted light off of a high-reflectivity surface or a low-reflectivity surface so as to distinguish sensor-on, sensor under-positioned, sensor over-positioned and sensor-off conditions, as described with respect to FIGS. 4A-D, above.

A reflection-detector sensor position indicator has been disclosed in detail in connection with various embodiments. These embodiments are disclosed by way of examples only and are not to limit the scope of the claims that follow. One of ordinary skill in art will appreciate many variations and modifications.

What is claimed is:

1. A physiological measurement system comprising:
a sensor having an attachment assembly configured to position emitters over a fingernail and to position a detector on a fingertip opposite the fingernail so that the emitters are positioned to transmit multiple wavelength light into the fingernail and so that the detector is positioned to detect the transmitted light after attenuation by pulsatile blood flow perfused within a fingernail bed underneath the fingernail and generate a sensor signal responsive to the intensity of the detected light; and
a physiological monitor in communications with the sensor so as to drive the emitters, receive the corresponding sensor signal from the detector and generate a display that depicts the position of a finger relative to the sensor.

2. The physiological measurement system according to claim 1 further comprising a second detector incorporated within the sensor that generates a sensor position signal responsive to the position of the emitters over the fingernail.

3. The physiological measurement system according to claim 2 further comprising a third detector incorporated within the sensor that generates a second sensor position signal responsive to the position of the emitters over the fingernail.

4. The physiological measurement system according to claim 1, wherein the physiological monitor is further configured to indicate a sensor under-positioned condition and a sensor over-positioned condition.

5. The physiological measurement system according to claim 1, wherein the physiological monitor is further configured to indicate a sensor on condition and a sensor off condition.

6. The physiological measurement system according to claim 1, wherein the physiological monitor indicates a sensor off misplaced condition using an audible alert.

7. A physiological monitor comprising:
a sensor input configured to receive and communicate with a sensor connector, the sensor having an attachment assembly configured to position emitters and at least one detector relative to a finger of a patient; and
a hardware processor which receives signals output from the sensor and generates a display that depicts the position of a finger relative to the sensor.

8. The physiological monitor of claim 7, wherein the at least one detector comprises at least two detectors and wherein at least one of the detectors generates a sensor position signal responsive to the position of the emitters over the finger.

9. The physiological monitor of claim 8, further comprising a third detector incorporated within the sensor that generates a second sensor position signal responsive to the position of the emitters over the finger.

10. The physiological monitor of claim 7, wherein the physiological monitor is further configured to indicate a sensor under-positioned condition and a sensor over-positioned condition.

11. The physiological monitor of claim 7, wherein the physiological monitor is further configured to indicate a sensor on condition and a sensor off condition.

12. The physiological monitor of claim 7, wherein the physiological monitor indicates a sensor off misplaced condition using an audible alert.

* * * * *